United States Patent
Matthiesen

(10) Patent No.: US 7,049,414 B2
(45) Date of Patent: May 23, 2006

(54) ISOLATION OF LECTINS

(75) Inventor: Finn Matthiesen, Brønshøj (DK)

(73) Assignee: Natimmune A/S, Copenhagen O (DK)

( * ) Notice: Subject to any disclaimer, the term of this patent is extended or adjusted under 35 U.S.C. 154(b) by 345 days.

(21) Appl. No.: 10/398,151

(22) PCT Filed: Oct. 18, 2002

(86) PCT No.: PCT/DK02/00698

§ 371 (c)(1),
(2), (4) Date: Apr. 2, 2003

(87) PCT Pub. No.: WO03/033522

PCT Pub. Date: Apr. 24, 2003

(65) Prior Publication Data

US 2004/0019186 A1   Jan. 29, 2004

(30) Foreign Application Priority Data

Oct. 19, 2001  (DK) .............................. 2001 01538

(51) Int. Cl.
*C07K 14/47* (2006.01)
*C07K 14/415* (2006.01)
*C07H 5/04* (2006.01)

(52) U.S. Cl. ...................... 530/396; 530/370; 530/536; 530/55.1

(58) Field of Classification Search .................... 435/6; 530/396, 370; 536/55.1
See application file for complete search history.

(56) References Cited

FOREIGN PATENT DOCUMENTS

| WO | WO9106010 | * 5/1991 |
| WO | WO0070043 | * 11/2000 |

OTHER PUBLICATIONS

Haurum, et al., Studies oon the carbohydrate-binding characteristics of human pulmonary surfactant-associated protein A and comparison with two other collections: mannan-binding protein and conglutinin, Biochem. J. vol. 293, pp. 873-878, 1993.

Kenneth et al., Structural Analysis of Monosaccharide Recognition by rat liver mannose-binding protein, J. Biol. Chem., vol. 271, pp 663-674, Jan. 1996.

(Continued)

*Primary Examiner*—Karen Cochrane Carlson
*Assistant Examiner*—Marsha Tsay
(74) *Attorney, Agent, or Firm*—Iver P. Cooper

(57) ABSTRACT

The invention relates to a process for isolating a lectin composition, in particular comprising the mannose-binding lectin (MBL), suitable for using recombinantly produced lectins as starting material, as well as methods for enriching a lectin preparation with respect to high molecular weight lectins. The method implies the use of sugar derivative modified solid supports, wherein the concentration of sugar derivatives on the solid support contributes to the isolation of predetermined oligomers of lectins.

47 Claims, 3 Drawing Sheets

OTHER PUBLICATIONS

Figure 1:
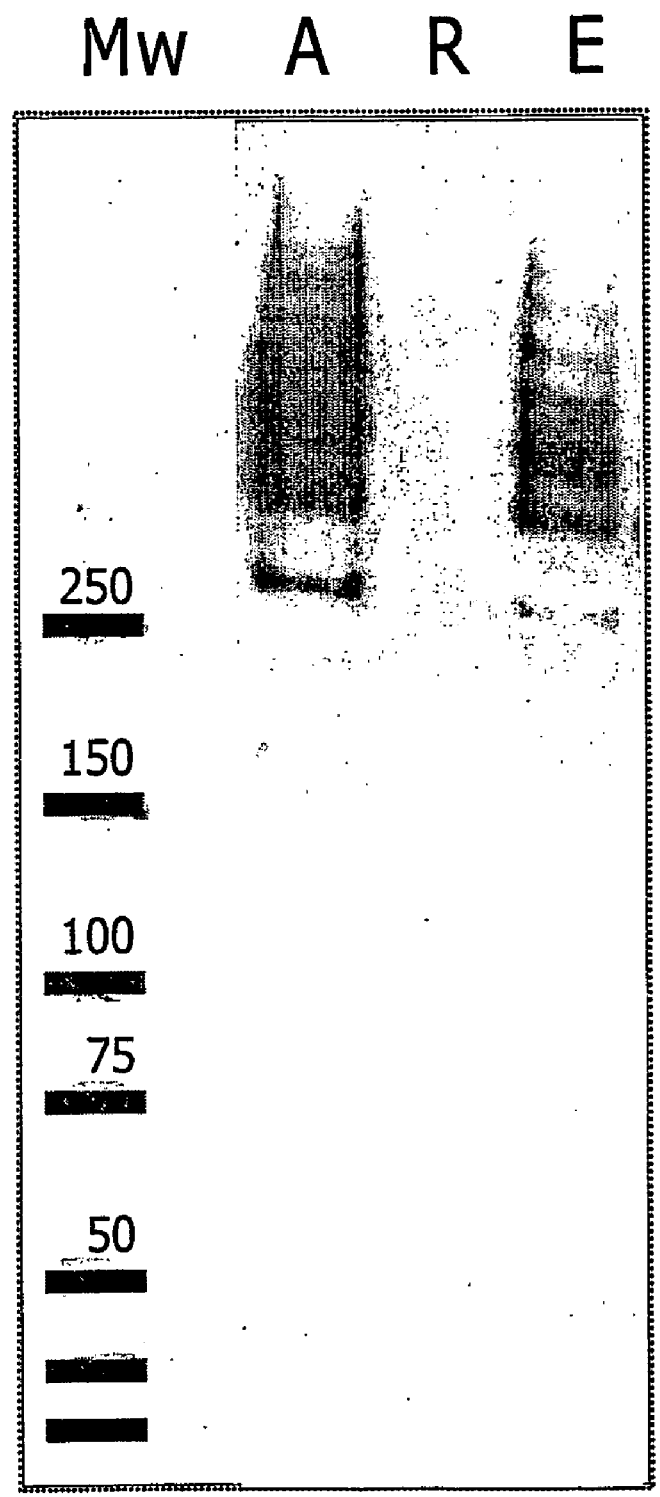

Blomberg, Lennart Arne, A process for the manufacture of a gel product, EP 0320472 A, Jun. 14, 1989.

Anion exchange resin for sepg. And concentrating boron isotope—contains amino-poly:ol gp., has high sepn. Coefft. And boric acid desorption., Database WPI, Week, Derwent Publications Ltd., London, GB, Class, AN Jun. 7, 1985-174418 & JP 60102947 A, Abstract.

Hydrophilic epoxy resin—by incorporating n-methyl adn/or n-ethyl glucosamine, Database WPO, Week, Derwent Publications ltd., London, GB, Class, AN 1973-21044U & JP 73011239, Jan. 18, 1991, Abstract.

Hartrum, et al., Antibiotic-metal complexes in the detection of gram-negative bacteria and other biological analytes, WO 0127628 A1, Apr. 19, 2001.

\* cited by examiner

ISOLATION OF LECTINS

CROSS REFERENCE TO RELATED APPLICATIONS

This application is filed under the provisions of 35 USC §371 based on International Application No. PCT/DK02/00698, filed on Oct. 18, 2002, which claims priority to Denmark Application No. PA 2001 01538 filed on Oct. 19, 2001, each of which is incorporated herein by reference.

The invention relates to a process for isolating a lectin composition, in particular comprising the mannose-binding lectin (MBL), suitable for using recombinantly produced lectins as starting material, as well as methods for enriching a lectin preparation with respect to high molecular weight lectins.

BACKGROUND OF THE INVENTION

Lectins are proteins characterized by the presence of a carbohydrate binding domain. Collectins are a group of lectins comprising an oligomeric structure of subunits, each subunit having a carbohydrate binding domain. In vivo lectins are represented in a variety of number of subunits leading to populations of lectins with different molecular mass.

MBL is a protein of the collectin family and characterized by an oligomeric structure of subunits each consisting of a calcium-dependent, C-type carbohydrate-recognition domain (CRD), attached to a collagenous rod. MBL activates the complement system via associated serine proteases (MASP—mannose-binding lectin associated serine proteases), i.e. by a mechanism similar to C1q. Mannose-binding protein (MBL) is a protein to be used for substitution or replacement therapy in patients with inherited or acquired MBL-deficiency associated with functional and/or clinical symptoms.

MBL derived from human blood plasma is assembled into an oligomer of subunits, each consisting of three identical polypeptide chains. The number of subunits in an MBL molecule is varying [Lipscombe R J, et al: Distinct physicochemical characteristics of human mannose binding protein expressed by individuals of differing genotype, Immunology 85 (1995) 660–667.], but it has been suggested that the biologically active polypeptide is an oligomer consisting of more than three subunits. Plasma comprises oligomers of more than three subunits as well as denatured and structurally impaired protein forms leading to bands on for example SDS gels between the dominating MBL bands corresponding to the higher oligomers.

Recombinantly produced MBL reveals an oligomer variation similar to plasma-derived MBL [Vorup-Jensen T et al: Recombinant expression of human mannan-binding lectin, Int. Immunopharm. 1 (2001) 677–687]. However, recombinantly produced MBL usually has a higher content of low-mass forms than plasma derived MBL. Low-mass forms of MBL include for example single polypeptide chains, single subunits, and dimeric subunits.

Lectins are typically isolated by applying a composition comprising the lectins to a column being modified with a sugar to which the lectins bind. However, the efficacy of the columns varies. In PCT application WO 00/70043 a method for separating high oligomers from low mass forms is described, wherein recombinantly produced MBL is subjected to fractionation on a special column, wherein the column as such does not have any affinity for the MBL.

DESCRIPTION OF THE INVENTION

A fast and simple method to isolate lectins, such as mannose-binding lectin (MBL), or derivatives and variants thereof (herein collectively designated lectins) from a solution is of major importance.

Moreover, to be in control of the mass distribution of lectins is also of major importance, because different oligomers of said lectin polypeptides possess different biological functions and activity.

The present invention describes a method to isolate lectins, such as MBL, by applying the preparation to a solid support having coupled thereto a predetermined concentration of a sugar derivative. The method can be used as a unit operation during preparation, purification, and/or formulation of said polypeptide. Compared to other methods, it is advantageous that the method of the invention can be applied to change the composition of oligomers of said polypeptide, so that high-mass oligomers of said polypeptide are separated from low-mass oligomers of said polypeptide, or intermediate-mass oligomers are separated from high-mass oligomers and low-mass oligomers.

Thus one objective of the present invention is to provide a method for isolating at least one lectin from a preparation comprising a variety of lectin molecules, comprising establishing a solid support having coupled thereto a predetermined concentration of a sugar derivative, applying the preparation to said solid support, allowing the lectins to bind to the sugar derivative coupled to the solid support, washing the solid support, with a washing liquid removing unbound contaminants, and optionally recovering said lectin(s) from the solid support.

By the term "predetermined concentration" is meant that a predetermined volume of sugar derivative having a predetermined concentration is applied to a predetermined volume or area of solid support allowing the sugar derivative to be coupled to the solid support. In one embodiment the term means that a predetermined concentration of sugar derivative is coupled to a predetermined volume or area of the solid support.

By the term "contaminant" is meant contaminants in the lectin preparation as well as lectins not being bound to the sugar derivative due to their smaller molecular weight. In particular when desiring intermediate molecular weight lectins, the contaminants may comprise the desired lectins when using two- or more step procedures as discussed below. Thus, the term "contaminant" is synonymous with unbound material including unbound lectins.

By the term "a variety of lectin molecules" is preferably meant a variety of oligomers of lectin molecules, said lectin molecules having identical or substantially identical structural subunits, such as described below.

It is a second objective of the present invention to provide such solid supports, having covalently coupled thereto a predetermined concentration of a sugar derivative, wherein the sugar derivative is preferably an amino sugar.

In another aspect the invention relates to a method for changing the oligomer distribution of lectins in solution. Hence, in one embodiment the invention relates to a method for increasing the ratio R of a composition comprising a variety of lectin molecules, wherein R is the ratio of the concentration of lectin molecules having a high molecular weight above a predetermined molecular weight to the concentration of lectin molecules having a low molecular weight below or equal to the predetermined molecular weight, said method comprising obtaining a lectin preparation comprising low molecular weight lectin and high molecular weight lectin, said preparation having the ratio $R=R_0$, applying the preparation to an isolation method, preferably the method for isolating at least one lectin from a preparation described herein above, obtaining a composition comprising the recovered lectin molecules.

Thereby a composition having an increased content of high mass oligomers of lectins as compared to the starting material is obtained.

In particular the increase of the ratio leads to compositions comprising lectins having a molecular weight above the molecular weight for dimer lectins. Thus, in another aspect the invention relates to a method for producing a composition comprising a variety of lectin molecules, wherein substantially all of said lectin molecules have a molecular weight above a predetermined molecular weight for dimer lectins, said method comprising, obtaining a lectin preparation comprising lectin molecules having a high molecular weight above the predetermined molecular weight and lectin molecules having a low molecular weight below or equal to the predetermined molecular weight, said preparation having the ratio $R=R_0$, wherein R is the ratio of the concentration of lectin molecules having a high molecular weight above the predetermined molecular weight to the concentration of lectin molecules having a low molecular weight below or equal to the predetermined molecular weight, applying the preparation to an isolation method, preferably the method for isolating at least one lectin from a preparation described herein above, obtaining a composition comprising the recovered lectin molecules.

Since the starting material for the methods comprises high mass lectins as well as low mass lectins, the invention also relates to a method for separating a composition comprising a variety of lectin molecules, wherein substantially all of said lectin molecules have a high molecular weight above a predetermined molecular weight, from a lectin preparation comprising lectin molecules having a high molecular weight above the predetermined molecular weight and lectin molecules having a low molecular weight below or equal to the molecular weight for dimer lectins, said preparation having the ratio $R=R_0$, wherein R is the ratio of the concentration of lectin molecules having a high molecular weight above the predetermined molecular weight to the concentration of lectin molecules having a low molecular weight below or equal to the predetermined molecular weight, said method comprising obtaining said lectin preparation, applying the preparation for an isolation method, preferably the method for isolating at least one lectin from a preparation described herein above, obtaining a composition comprising the recovered lectin molecules.

For most purposes the high mass lectins are the desired ones; however, for some applications the low mass lectins are wanted, and accordingly, the invention further relates to a method for producing a composition comprising a variety of lectin molecules, wherein substantially all of said lectin molecules have a low molecular weight below or equal to a predetermined molecular weight, said method comprising, obtaining a lectin preparation comprising lectin molecules having a high molecular weight above the predetermined molecular weight and lectin molecules having a low molecular weight below or equal to the predetermined molecular weight, said preparation having the ratio $R=R_0$, wherein R is the ratio of the concentration of lectin molecules having a high molecular weight above the predetermined molecular weight to the concentration of lectin molecules having a low molecular weight below or equal to the predetermined molecular weight, applying the preparation to an isolation method, preferably the method for isolating at least one lectin from a preparation described herein above, obtaining a composition comprising the unbound lectin molecules of the washing liquid.

For all the methods mentioned above, preferably the composition of recovered lectin molecules has the ratio $R=R_1$, wherein $R_1$ is at least 1, such as at least 1.05, such as at least 1.10, such as at least 1.15, such as at least 1.25, such as at least 1.50, such as at least 1.75, such as at least 2.0, such as at least 2.5, such as at least 3.0, such as at least 4.0, such as at least 5.0, such as at least 6.0, such as at least 7.0, such as at least 8.0, such as at least 9.0, such as at least 10.0, such as at least 15, such as at least 20, such as at least 30, such as at least 40, such as at least 50, such as at least 60, such as at least 70, such as at least 80, such as at least 90, such as at least 100, such as at least 100, such as at least 1000, such as at least 10000.

For all of the methods disclosed above, the predetermined molecular weight is preferably the molecular weight for dimer lectins, more preferred for trimer lectins.

For most purposes high mass lectins are the desired ones; however, in certain embodiments intermediate mass lectins may be wanted. Accordingly, in a further aspect the present invention relates to a method of increasing the ratio R of a composition comprising a variety of lectin molecules, wherein R is the ratio of the concentration of lectins having an intermediate molecular mass to the concentration of lectin molecules having a high molecular mass and a low molecular mass, wherein intermediate molecular mass is a molecular weight below a first predetermined molecular weight and above a second predetermined molecular weight, high molecular mass is a molecular mass above or equal to the first predetermined molecular weight, and low molecular mass is a molecular mass below or equal to the second predetermined molecular weight, said method comprising the steps of obtaining a lectin compostion comprising low molecular mass lectin, intermediate molecular mass lectin and high molecular mass lectin, said preparation having the ratio $R=R_0$, applying the composition to an isolation method, preferably the method for isolating at least one lectin from a preparation described herein above; and obtaining a composition comprising the recovered lectin molecules; and optionally repeating the step of applying the composition to an isolation method, preferably the method for isolating at least one lectin from a preparation described herein above.

In one embodiment the first predetermined molecular weight may be the molecular weight for heptamer lectins, and the second predetermined molecular weight is the molecular weight for dimer lectins.

In another aspect the invention relates to a method for isolating at least one lectin from a preparation comprising a variety of lectin molecules, comprising establishing a solid support being derivatized with at least one amino sugar, applying the preparation to said solid support, allowing the lectins to bind to the amino sugar coupled to the solid support, washing the solid support with a washing liquid removing unbound contaminants, and optionally recovering said lectin(s) from the solid support.

By the term "derivatized" is meant that the amino sugar is coupled to the solid support as described above.

The lectin according to the invention may be any lectin wherein several oligomeric forms are produced, for example collectins, such as mannose-binding lectins. In particular the invention relates to a method for producing MBL compositions. By the term MBL is meant mannose-binding lectin (or mannose-binding protein, as denoted by some authors). MBL is preferably human MBL having a protein sequence as shown in for example PCT application WO 00/70043 or derivatives or variants thereof being functional equivalents of MBL. In the following the invention will be described in relation to the lectin MBL.

The methods according to the present invention allow large scale manufacturing of the lectins in question. Thus, in another aspect the invention relates to any industrial or large scale method of manufacturing MBL comprising the application of said methods during the manufacturing of said MBL.

DRAWINGS

FIG. 1 illustrates the eluting profile of recombinantly produced MBL applied on and eluted from a column with immobilized D-mannosamine as described in example 1. The figure shows an SDS-PAGE Western using monoclonal antibodies raised against plasma derived MBL. MW=marker (kDa), A=Application (recombinantly derived MBL from before use of the invention), R=Run Through fraction obtain during application; E=Eluting fraction after wash with EDTA (recombinantly derived MBL after use of the invention).

Figure 2:
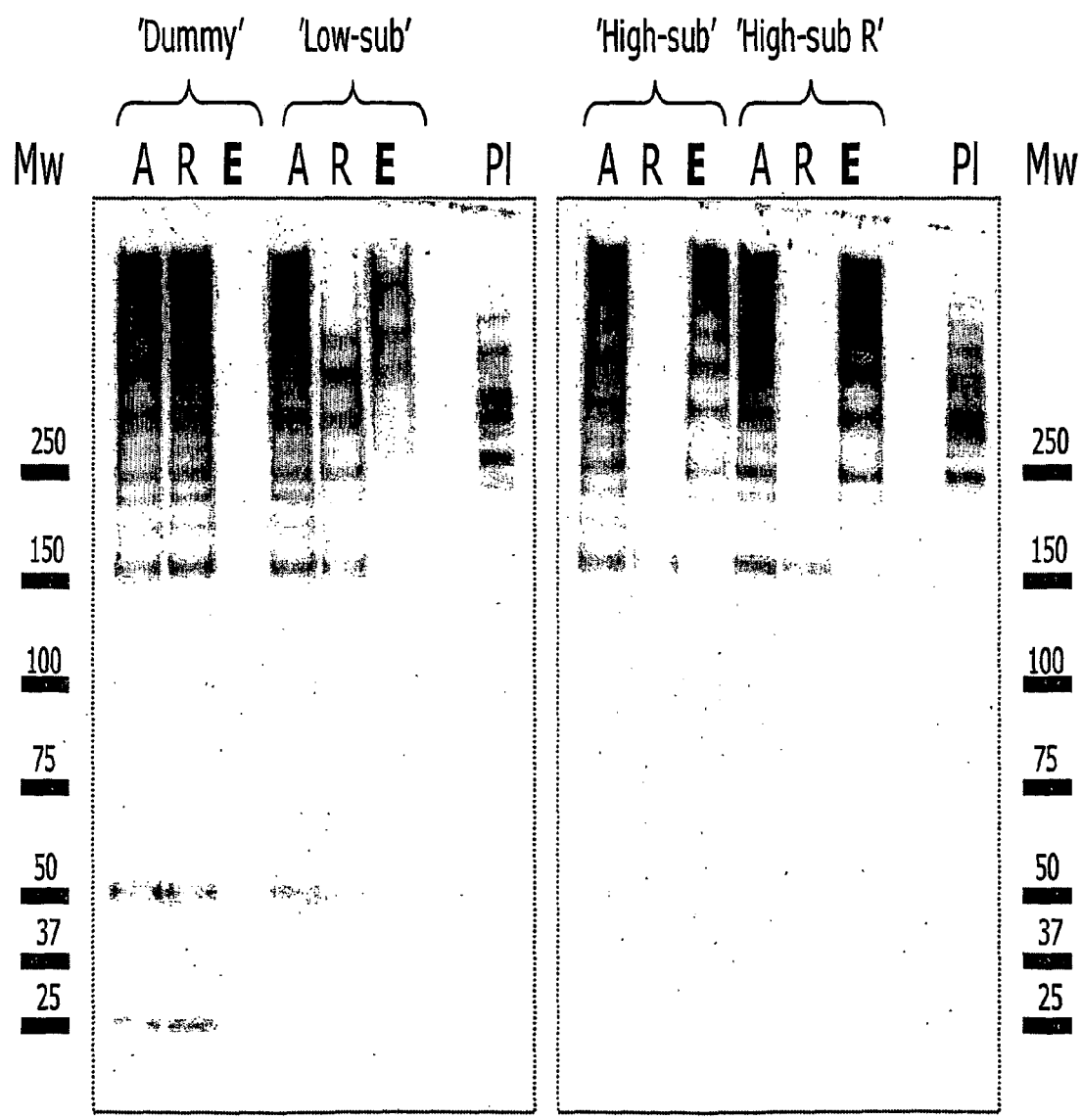

FIG. 2 illustrates the eluting profile of recombinantly produced MBL applied on and eluted from a column with immobilized D-mannosamine as described in example 2. The figure shows an SDS-PAGE Western using monoclonal antibodies raised against plasma derived MBL. 'Dummy': Column coupled with no amino sugar, 'Low-sub'=column coupled with low amount of amino sugar, 'High-sub'=column coupled with large amount of amino sugar, 'high-sub R'=column coupled with large amount of amino sugar, after regeneration with NaOH. MW=marker (kDa), A=Application, R=Run Through fraction obtain during application; E=Eluting fraction after wash with EDTA, Pl=Plasma derived MBL (control).

Figure 3:
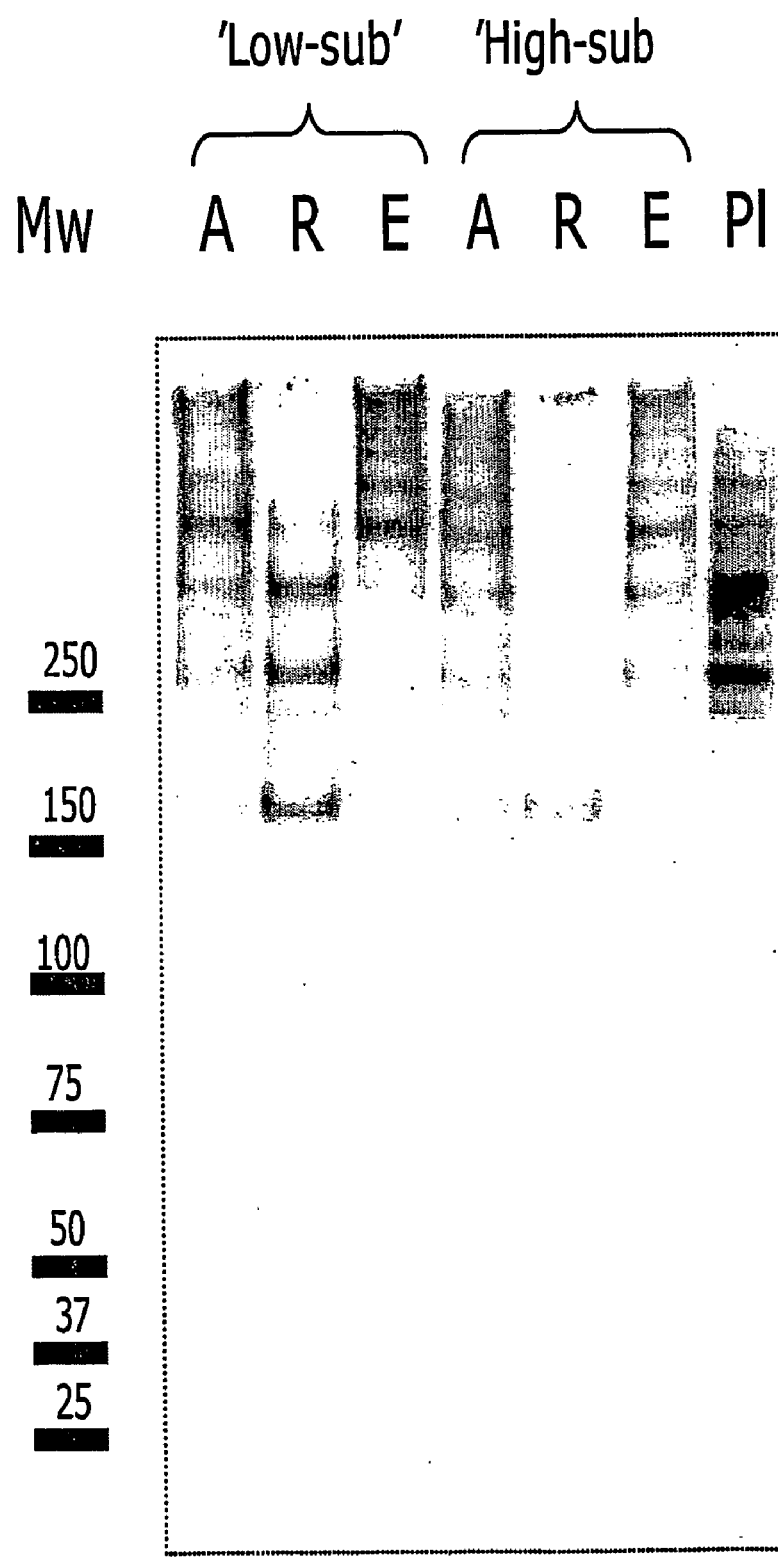

FIG. 3 illustrates the eluting profile of recombinantly produced MBL applied on and eluted from a column with immobilized D-glucosamine in two concentrations as described in example 5. The figure shows an SDS-PAGE Western using monoclonal antibodies raised against plasma derived MBL. A=Application (recombinantly derived MBL from before use of the invention), R=Run Through fraction obtain during application; E=Eluting fraction after wash with EDTA (recombinantly derived MBL after use of the invention), Pl=Plasma derived MBL (control).

DETAILED DESCRIPTION OF THE INVENTION

Sugar Derivative

In a preferred embodiment the term sugar derivative means a compound derived from a sugar, wherein the derived compound possesses the capability of being coupled to the solid support in a predetermined oriented manner. The present inventors have identified one of the reasons why previous isolation methods may lack in efficiency. It has thus been found that lectins bind to specific binding sites on the saccharides, and when the prior art uses sugars coupled to column and other solid supports in a random manner, a percentage of the saccharides coupled are not capable of binding the lectins since the binding sites are not positioned in order to bind the lectin.

Thus, the sugar derivative according to the present invention preferably comprises a reactive group that allows oriented coupling to the solid support. The sugar derivative may be any derivative capable of binding the lectin when the sugar derivative is coupled to the solid support. Sugar derivatives not capable of binding the lectin, when the derivative is in free form, i.e. un-coupled, may also be used according to the invention, when capable of binding the lectin in coupled form.

The predetermined orientation of the sugar may be obtained by incorporating a reactive group into the sugar, preferably at a specific position, whereby it is possible to couple the sugar derivative to the solid support in a specifically oriented manner, in that the coupling takes place through the reactive group to the solid support. Thus, by the term "oriented coupling" is meant that the sugar is coupled to the solid support through a specific, predetermined group in the sugar molecule, so that the free part of the sugar molecule is oriented in a predetermined position.

In a monosaccharide the binding site and the reactive group are positioned in the same monosaccharide structure; however, in disaccharides and higher oligosaccharides and polysaccharides, the binding site may be positioned in another monosaccharide structure than the reactive group. In the present context the term "monosaccharide structure" means the structure capable of forming a ring in the saccharide. For example, a disaccharide comprises two monosaccharide structures. In a preferred embodiment the reactive group is positioned far from the binding site thereby obtaining the best possibilities of having a binding site not sterically hindered.

Sugars

The term sugar derivative means any compound being derived from a sugar. In the present context sugar means any carbohydrate, including monosaccharides, disaccharides, trisaccharides, oligosaccharides, and polysaccharides, whether being a five-membered ring (pentose) or a six-membered ring (hexose) or combinations thereof, or whether being a D-form or an L-form, as well as substances derived from monosaccharides by reduction of the carbonyl group (alditols), by oxidation of terminal groups to carboxylic acids, or by replacement of hydroxy groups by another group. It also includes derivatives of these compounds.

Monosaccharides include polyhydroxy aldehydes $H-[CHOH]_n-CHO$ and polyhydroxy ketones $H-[CHOH]_n-CO-[CHOH]_m-H$, i.e. aldoses, dialdoses, aldoketoses, ketoses, diketoses, deoxy sugars, amino sugars, and their derivatives.

Aldoses include monosaccharides with an aldehydic carbonyl, i.e. polyhydroxy aldehydes $H-[CHOH]_n-CHO$. Aldoses also include monosaccharides with a potential aldehydic carbonyl group—a hemiacetal group—which arises from the ring closure of the aldose.

Ketoses include monosaccharides with a ketonic group, i.e. polyhydroxy ketones $H-[CHOH]_n-CO-[CHOH]_m-H$, i.e. ketones also include monosaccharides with a potential ketonic carbonyl group—a hemiketal group—which arises from the ring closure of the ketose.

Pyranoses are cyclic hemiacetals or cyclic hemiketals with a tetrahydrofuran (five-membered ring).

Furanoses are cyclic hemiacetals or cyclic hemiketals with a tetrahydrofuran (five-membered ring).

Dialdoses, diketoses, ketoaldoses (aldoketoses, aldosuloses), alditols are monosaccharides with more than one aldehyde and/or ketone.

Aldonic acids, ketonic acids are aldoses in which the aldehyde group has been exchanged with a carboxy group.

Examples of derivatives of the sugars are uronic acids, aldoses, in which the first $CH_2OH$-group has been exchanged with a carboxy group; aldaric acids, aldonic acids, in which the first $CH_2OH$-group has been exchanged with a carboxy group; deoxy sugars, monosaccharides, in which a hydroxyl group has been exchanged with a hydrogen; amino sugars, monosaccharides, in which a hydroxyl group has been exchanged with an amino group.

Also glycosylamines are included, being amino sugars, in which the hydroxyl group on the hemiacetal group (formed after ring closure) has been exchanged with an amino group.

In the present context the term acetal is used in its normal meaning, i.e. monosaccharides arising from ring closure of the aldose or ketose. Furthermore, glycosides are acetals arising from elimination of water between the hemiacetal and hemiketal hydroxy group of a monosaccharide, oligosaccharide and polysaccharide, and the hydroxy group of another monosaccharide, oligosaccharide and polysaccharide. A glydosidic bond is the bond between the monosaccharides in a glycoside.

In the present context the term sugar, or any of the saccharides and derivatives mentioned herein, includes all the various steric forms of the sugars, including the D-form and the L-form, α-form, and β-form. Thus, as an example, mannosamine means mannosamine in any of the steric forms, including D-mannosamine, L-mannosamine and (D,L)-mannosamine. Only when a specific steric form is used is this mentioned as for example the D-mannosamine.

Specific Derivatives

The invention relates in particular to sugar derivatives having a reactive group selected from amino groups, wherein the amino group may for example be selected from the group consisting of primary amino groups, secondary amino groups and tertiary amino groups.

In particular the invention relates to the use of amino sugars as the sugar derivative. The amino sugars may be amino monosaccharides, amino disaccharides, amino oligosaccharides, and amino polysaccharides, wherein at least one amino group is incorporated in a manner allowing it to act as a reactive group when coupling the amino sugar to the solid support.

Examples of suitable amino monosaccharides are:

Amino aldoses, such as mannosamine, glucosamine, allosamine, altrosamine, ribosamine, arabinosamine, gulosamine, idosamine, galactosamine, talosamine, xylosamine, lyxosamine. In particular D-mannosamine, D-glucosamine, D-allosamine, D-altrosamine, D-ribosamine, D-arabinosamine, L-gulosamine, L-idosamine, L-galactosamine, L-talosamine, L-xylosamine, L-lyxosamine.

Amino ketoses, such as sorbosamine, tagatosamine, psicosamine, fructosamine. In particular D-sorbosamine, D-tagatosamine, L-psicosamine, L-fructosamine.

Amino deoxyaldoses, such as derivatives of fucose, for example fucosamine and fucosylamine, preferably L-fucosamine.

In particular in relation to isolation of MBL, the following examples of amino sugars are suitable: mannosamine, glucosamine, galactosamine, fructosamine. In particular D-mannosamine, D-glucosamine, L-galactosamine, L-fucosamine.

More preferably the amino sugars selected from the group consisting of glucosamine and mannosamine, most preferably amino sugars selected from the group consisting of L-fucosamine, D-glucosamine and D-mannosamine may be used, in particular D-glucosamine and D-mannosamine. The formula of D-mannosamine is indicated herein below as free D-mannosamine and as D-mannosamine bound to a resin.

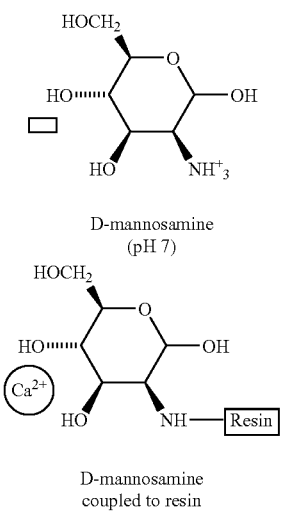

D-mannosamine
(pH 7)

D-mannosamine
coupled to resin

Also disaccharides, oligosaccharides, and polysaccharides having an amino group positioned as a reactive group in one part of the molecule, and a lectin binding site, in particular a MBL binding site in another part of the molecule may be used.

For example the amino sugar may be any disaccharide derivative comprising an amino group, wherein at least one of the monosaccharide subunits of the disaccharide is selected from the group consisting of mannose and glucose. Examples of preferred disaccharides include saccharose derivatives, such as saccharosamine, and maltose derivatives, such as maltosamine, comprising an amino group, as well as agarosamine, cellulosamine, and amylosamine. A preferred disaccharide derivative is saccharosamine.

Furthermore the amino sugar may for example be a multimer of glucosamine, such as a glucosamine dimer, a glucosamine oligomer or a glucosamine polymer.

Solid Support

The solid support may be any support used for capturing and/or isolating lectins. Thus the solid support may be any columns, filters or particles used for isolation and purification, such as chromatographic resins, and magnetic particles.

Also, the solid support may be a surface capable of binding the lectin for example for further analyses, such as plastic surfaces and glass surfaces. Plastic surfaces may for example be selected from the group consisting of microtiter plates, ELISA wells and activated microtiter plates. Activated microtiter plates may for example be cyanuric chloride activated Covalink™ NH$_2$ Primary Amine from Life Technologies.

In one embodiment of the present invention, any solid support capable of covalently binding amines, preferably primary amines, may be used with the invention.

Useful columns may be any of the columns selected from the group consisting of N-N-hydroxy succinimide activated resins (for example NHS-Sepharose 4 FF from APBiotech, Affi-Gel 10 from BioRad, Affi-Gel 15 from BioRad or Affi-Prep from BioRad), cyanogen bromide activated resins (for example CNBr-activated Sepharose 4 FF from APBiotech), ECH Sepharose 4B from APBiotech, Activated CH-Sepharose 4B from AP-Biotech and epoxy activated resins (such as Epoxy-activated Sepharose 6B) as well as their corresponding cross-linked resins.

A predetermined concentration of a sugar derivative may be coupled to the solid support according to the present invention. The predetermined concentration of the sugar derivative should be selected according to what predetermined molecular weight is desirable for the particular embodiment of the present invention.

The sugar derivative concentration is determined by two factors:
1) concentration of positions (ligand arms) on the solid support capable of coupling a sugar derivative,
2) concentration of sugar derivative per ligand arms.

The concentration of ligand arms per volume solid support is mostly determined by the production process of the solid support, and may be controlled by coupling a labelled ligand to the solid support.

The concentration of sugar derivative per ligand arms is regulated by regulating the volume and concentration of sugar derivative allowed to couple to the ligand arms.

In general a high predetermined concentration of sugar derivative is used when a relatively low predetermined molecular weight is desirable, and a low predetermined concentration of sugar derivative is used when a relatively high predetermined molecular weight is desirable.

The predetermined concentration of sugar derivative may for example be determined by the amount of sugar derivative coupled to a specific amount of solid support. For example, when the solid support is a chromatography column resin, the predetermined concentration of monosaccharide derivative is preferably from 0.1 mg sugar derivative per ml resin to 1000 mg sugar derivative per ml resin, more preferably between 0.5 mg sugar derivative per ml resin and 500 mg sugar derivative per ml resin, even more preferably from 2 mg sugar derivative per ml resin to 100 mg sugar derivative per ml resin.

In the present context a standard for the solid support is a cross-linked Sepharose resin modified with N-hydroxysuccinimide (NHS) residues, as described in the Examples. Preferably from 15–25 µmol ligand arm per ml drained resin is used. Such a solid support is specified to be able to bind 5 µmol dipeptide per ml drained resin, or 1–2 µmol alfa-chymotrypsinogen per ml drained resin.

From this standardised solid support, intervals for the predetermined concentration of sugar derivative to be coupled to the resin in order to obtain the lectins desired from the variety of lectins are given.

Isolation of high molecular lectins as defined herein to be above the molecular weight for dimer lectins is obtained using the standard column having coupled thereto a sugar derivative in a predetermined concentration of from 10 µmol per ml drained resin to 100 µmol per ml drained resin, such as from 20 µmol per ml drained resin to 80 µmol per ml drained resin, such as from 30 µmol per ml drained resin to 70 µmol per ml drained resin, such as from 40 µmol per ml drained resin to 60 µmol per ml drained resin. For monosaccharides said concentrations correspond to from 2 mg per ml drained resin to 20 mg per ml drained resin, such as from 4 mg per ml drained resin to 16 mg per ml drained resin, such as from 6 mg per ml drained resin to 14 mg per ml drained resin, such as from 8 mg per ml drained resin to 12 mg per ml drained resin.

Isolation of high molecular lectins as defined herein to be above the molecular weight for trimer lectins is obtained using the standard column having coupled thereto a sugar derivative in a predetermined concentration of from 10 µmol per ml drained resin to 80 µmol per ml drained resin, such as from 20 µmol per ml drained resin to 70 µmol per ml drained resin, such as from 30 µmol per ml drained resin to 70 µmol per ml drained resin, such as from 40 µmol per ml drained resin to 60 µmol per ml drained resin.

Isolation of high molecular lectins as defined herein to be above the molecular weight for tetramer lectins is obtained using the standard column having coupled thereto a sugar derivative in a predetermined concentration of from 10 µmol per ml drained resin to 60 µmol per ml drained resin, such as from 20 µmol per ml drained resin to 60 µmol per ml drained resin, such as from 30 µmol per ml drained resin to 50 µmol per ml drained resin.

A high ligand solid support capable of binding also low molecular weight lectins, such as dimer lectins, is produced by using the standard column having coupled thereto a sugar derivative in a predetermined concentration of above 200 µmol per ml drained resin, such as from above 300 µmol per ml drained resin, such as from above 400 µmol per ml drained resin, such as from above 500 µmol per ml drained resin.

Washing Liquid

The washing liquid according to the present invention may be any suitable washing liquid known to the person skilled in the art. In particular the buffer may comprise one or more components capable of interfering with the association between the lectin and the sugar derivative, such as the amino sugar.

In one embodiment of the present invention, the washing liquid comprises one or more components selected from the group consisting of sugars capable of binding to the lectin, sugar derivatives capable of binding to the lectin and divalent metal ion chelating agents.

Sugars and/or sugar derivatives capable of binding to the lectin may for example be any monosaccharide and/or monosaccharide derivative capable of binding to the lectin. For example any sugar derivative useful for coupling to the solid support according to the present invention (see herein above) or a corresponding non-derivatised sugar, or a corresponding sugar, which is further modified may be comprised within the washing liquid.

Such monosaccharides may for example be selected from the group consisting of mannose, N-acetylmannosamine, glucose, N-acetylglucosamine, frucose, N-acetylfrucosamine, galactose and N-acetylgalactosamine. In particular, the monosaccharides may be selected from the group consisting of D-glucose, D-mannose, L-fucose and L-galactose.

Sugars and/or sugar derivatives capable of binding to the lectin may also be any disaccharide, disaccharide derivative, trisaccharide, trisaccharide derivative, oligosaccharide, oligosaccharide derivative, polysaccharide or polysaccharide derivative wherein at least part the sugar is capable of binding to the lectin. Examples of useful oligosaccharides include but are not limited to saccharose and maltose.

Divalent metal ion chelating agents are any agents capable of chelating a divalent metal ion. The divalent metal ion may for example be Ca2+. Examples of divalent metal ion chelating agents include but are not limited to EDTA and citrate.

Furthermore the washing liquid may be prepared in any other manner suitable for elution of lectins known by the person skilled in the art. For example the washing liquid may comprise a high salt concentration or an acidic pH.

Lectins

The lectins isolated according to the present invention may be any lectins. For example the lectin may be a collectin, such as for example MBL (mannose-binding lectin), SP-A (lung surfactant protein A), SP-D (lung surfactant protein D), BK (or BC, bovine conglutinin) and CL-43 (collectin-43). Collectins all exhibit the following architecture: they have an N-terminal cysteine-rich region that appears to form inter-chain disulfide bonds, followed by a collagen-like region, an α-helical coiled-coil region and finally a C-typ lectin domain which is the pattern-recognizing region and is referred to as the carbohydrate recognition domain (CRD). The name collectin is derived from the presence of both collagen and lectin domains. The α-helical coiled-coil region initiates trimerisation of the individual polypetides to form collagen triple coils, thereby generating collectin subunits each consisting of 3 individual polypeptides, whereas the N-terminal region mediates formation of oligomers of subunits. Different collectins exhibit distinctive higher order structures, typically either tetramers of subunits or hexamers of subunits.

In a preferred embodiment of the present invention, the lectin is MBL or ficolin; in a more preferred embodiment the lectin is MBL.

The term lectins may be naturally occurring lectins as well as variants thereof, such as mutants, said variants being capable of binding a sugar.

In particular the invention is suitable for isolating MBL, which will be discussed more thoroughly in the following as an example of the invention, and not as a limitation of the invention.

Lectins according to the present invention may comprise one or more subunits. In particular collectins such as MBL may comprise one or more subunits, and each subunit of a collectin is normally consisting of 3 individual polypeptides. For example collectins such as MBL may be monomers, dimers, trimers, tetramers, pentamers, hexamers, heptamers, octamers, nonamers, decamers, 11-mers, 12-mers of subunits or collectins such as MBL may comprise even more than 12 subunits.

Composition

The ratio R discussed herein may be calculated using any suitable method. In a preferred embodiment a quantitative estimate of the R value of a in a sample might be done as follows:

The SDS-PAGE immunoblot is scanned into a TIFF file, or another non-compressed bitmap file. The pixel density along the sample bands are measured in a picture evaluation program, such as Scion Image for Windows 4.0 (Scion Corporation, freeware beta version on www.scioncorp.com), and exported to a data evaluation program (like Excel).

The migration corresponding to the predetermined molecular weight is settled from the migration of markers. In a preferred embodiment the predetermined molecular weight is the molecular weight of the dimeric lectin (for MBL about 200 kDa), and accordingly the migration corresponding to the dimeric lectin may be settled from the migration of markers (for example Precision Protein Standards, BioRad). The R value is calculated as the total pixel signal above reference migration point (for dimeric MBL 200 kDa), divided by the total pixel signal beneath the reference migration point (for dimeric MBL 200 kDa). $R_0$ is defined as the ratio in the starting material, while $R_1$ is the ratio along the corresponding evaluation line in the lectin sample recovered after the performance of a method according to the present invention.

The degree of increase of the ratio R depends on the starting material having ratio $R_0$, the starting material being the lectin preparation, for example an MBL preparation. It is preferred that at least 50% of the high molecular weight lectin of the composition has a molecular weight above the molecular weight for dimer lectins, preferably above the molecular weight for trimer lectins. When the lectin is MBL, it is thus preferred that at least 50% of the high molecular weight MBL of the composition has a molecular weight above 200 kDa, such as above 225 kDa, such as above 250 kDa, such as above 300 kDa.

By producing an MBL composition according to the present invention, the MBL composition is preferably substantially free from any impurities naturally associated with the MBL when produced in a native host organism, for example impurities associated with MBL, when MBL is purified from plasma MBL.

The method may be used for producing high mass MBL compositions from any MBL source, such as any mammalian recombinant MBL or from plasma. However, the MBL source is preferably recombinant MBL, more preferably the MBL of the composition is human, such as MBL wherein the MBL subunit is assembled of three peptide sequences comprising the sequence as shown in SEQ ID NO:1 in PCT application WO 00/70043 or a functional equivalent thereof.

Recombinant Production

Although the method may be applied to any lectin starting material having both low and high mass lectin, such as MBL, it is particularly suitable for producing high mass lectin, such as MBL from a recombinantly produced preparation.

Thus, the MBL preparation is preferably a recombinant preparation, wherein the MBL preparation is obtained by
preparing a gene expression construct encoding human MBL peptide or a functional equivalent thereof,
transforming a host cell culture with the construct,
cultivating the host cell culture in a culture medium, thereby obtaining expression and secretion of the polypeptide into the culture medium,
obtaining a preparation comprising a variety of MBL molecules According to the invention, the sequences from the MBL gene may be from the human MBL gene or from MBL genes of other animal species, in which the immune system in this respect is acting like the human immune system. An example of a preferred embodiment of a preparation of a recombinant MBL according to the invention is described in example 1 of PCT application WO 00/70043 which is incorporated herein by reference. In the example the recombinant MBL is prepared by the use of an expression vector comprising sequences from the human MBL gene.

The invention also concerns the use of expression vectors comprising sequences which are functional derivatives of the sequences of the human MBL gene. By said functional derivatives are meant sequences containing base pair alterations that lead to no functional or essentially no functional differences of the expression vector, and the MBL prepared in this way has a functionality comparable to the MBL prepared by the use of an expression vector comprising the unaltered sequences from the human MBL gene.

In addition to the purification method, it is preferred that the gene expression construct and the host cell also favour production of higher oligomers. Accordingly, the gene expression construct preferably comprises at least one intron sequence from the human MBL gene or a functional equivalent thereof. Furthermore, the gene expression construct may comprise at least two exon sequences from the human MBL gene or a functional equivalent thereof. More preferably the gene expression construct comprises at least three exon sequences from the human MBL gene or a functional equivalent thereof. When comprising more than one exon, the exon sequences are preferably aligned as in the human MBL gene.

Although preferred that the sequence comprises intron sequences, it may for some applications be convenient that the expression construct comprises a cDNA sequence encoding a MBL subunit or a functional equivalent thereof.

The invention features the use of MBL gene expression constructs rather than MBL cDNA constructs for expression of rMBL in mammalian cell lines or transgenic animals to obtain recombinant MBL with structural properties under non-denaturing and denaturing conditions being substantially similar to natural human MBL. By "recombinant human MBL" is meant human MBL which is expressed from engineered nucleic acids, and by "MBL gene expression constructs" is meant an expression vector suitable for expression in mammalian cell lines and containing exon sequences and at least one intron sequence from the human MBL gene or from MBL genes of other animal species, such as but not limited to chimpanzees and rhesus monkeys.

Preferably, the DNA sequences encode a polypeptide sequence as shown in SEQ ID NO:1 of patent application WO 00/70043 or a functional equivalent, whereby a functional equivalent is as defined above. SEQ ID NO:1 corresponds to the MBL sequence having database accession NO: P11226. The equivalent may be obtained by a modification of the peptide sequence shown as SEQ ID NO:1, such as a sequence processing a corresponding property as the sequences mentioned in the present invention, but wherein one or more amino acids have been substituted with others. Preferably a functional equivalent contains conservative substitutions, i.e. where one or more amino acids are substituted by an amino acid having similar properties, such that a person skilled in the art of protein chemistry will expect the secondary and tertiary structure of the protein to be unchanged. Amino acids suitable for conservative substitutions include those having functionally similar side chains. For example, hydrophobic residues, e.g. glycine, alanine, valine, leucine, isoleucine and methionine, may replace another such residue. Similarly, conservative substitutions may involve interchanging hydrophilic residues: (e.g.: arginine and lysine, glutamine and aspargine, threonine and serine), basic reduces (e.g., lysine, arginine and histidine), and/or acidic residues (e.g., aspartic acid and glutamic acid). Functional equivalents may also, or alternatively, be modified by for example the deletion or addition of amino acids, or the chemical modification of amino acids, as long as the function of the polypeptide is preserved.

The isolated MBL peptide, including any functional equivalents thereof, may in one embodiment comprise at least 80 amino acid residues, such as at least 100 amino acid residues, such as at least 150 amino acid residues, such as at least 200 amino acid residues, for example at least 220 amino acid residues, such as at least 250 amino acid residues.

In a preferred embodiment the expression vector is suitable for expression in mammalian cell lines or transgenic animals which contain exon sequences and at least one intron sequence from the human MBL gene or from MBL genes of other animal species, such as, but not limited to, chimpanzees and rhesus monkeys. In one embodiment the host cell culture is cultured in a transgenic animal. By a transgenic animal in this context is meant an animal which has been genetically modified to contain and express the human MBL gene or fragments or mimics hereof.

In a preferred embodiment the expression construct of the present invention comprises a viral based vector, such as a DNA viral based vector, an RNA viral based vector, or a chimeric viral based vector. Examples of DNA viruses are cytomegalovirus, Herpex Simplex virus, Epstein-Barr virus, Simian virus 40, Bovine papillomavirus, Adeno-associated virus, Adenovirus, Vaccinia virus, and Baculo virus.

In mammalian host cells, a number of viral-based expression systems may be used. In cases where an adenovirus is used as an expression vector, the nucleic acid molecule of the invention may be ligated to an adenovirus transcription/translation control complex, for example, the late promoter and tripartite leader sequence. This chimeric gene may then be inserted into the adenovirus genome by in vitro or in vivo recombination. Insertion into a non-essential region of the viral genome (for example, region E1 or E3) will result in a recombinant virus that is viable and capable of expressing an MASP-3 gene product in infected hosts (for example, see Logan and Shenk, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

Examples of RNA virus are Semliki Forest virus, Sindbis virus, Poko virus, Rabies virus, Influenza virus, SV5, Respiratory Syncytial virus, Venezuela equine encephalitis virus, Kunjin virus, Sendai virus, Vesicular stomatitis virus, and Retroviruses.

Examples of chimetic viruses are Adenovirus, Sindbis virus and Adenovirus—adeno-associated virus.

Regarding specific vectors, reference is made to Makrides, S. C., "Components of vectors for Gene Transfer and Expression in Mammalian Cells", which is hereby incorporated by reference.

In particular, an Epstein-Barr virus origin of replication or functional derivatives or mimics hereof including the pREP9 vector is used.

In one aspect the invention provides an expression construct encoding human MBL, featured by comprising one or more intron sequences from the human MBL gene including functional derivatives hereof. Additionally, it contains a promoter region selected from genes of virus or eukaryotes, including mammalian and insects.

The promoter region is preferably selected to be different from the human MBL promoter, and preferably in order to optimize the yield of MBL and size distribution of MBL oligomers, the promoter region is selected to function most optimally with the vector and host cells in question.

In a preferred embodiment the promoter region is selected from a group comprising Rous sarcoma virus long terminal repeat promoter, and cytomegalovirus immediate-early promoter, and elongation factor-1 alpha promoter.

In another embodiment the promoter region is selected from genes of microorganisms, such as other viruses, yeasts and bacteria.

In order to obtain a greater yield of recombinant MBL, the promoter region may comprise enhancer elements, such as the QBI SP163 element of the 5' end un-translated region of the mouse vascular endothelian growth factor gene. The construct is used for transforming a host cell to obtain a host cell culture capable of expressing MBL. The host cell culture is preferably a eukaryotic host cell culture. By transformation of an eukaryotic cell culture is in this context meant introduction of recombinant DNA into the cells. The expression construct used in the process is characterised by having the MBL encoding region selected from mammalian genes including human genes and genes with big resemblance herewith such as the genes from the chimpanzee. The expression construct used is furthermore featured by the promoter region being selected from genes of virus or eukaryotes, including mammalian cells and cells from insects.

The process for producing recombinant MBL according to the invention is characterised in that the host cell culture is preferably eukaryotic, and for example a mammalian cell culture. A preferred host cell culture is a culture of human kidney cells, and in an even more preferred form the host cell culture is a culture of human embryonal kidney cells (HEK cells). The invention features the use of HEK 293 cell lines for production of recombinant human MBL. By "HEK 293 cell lines" is meant any cell line derived from human embryonal kidney tissue such as, but not limited to, the cell lines deposited at the American Type Culture Collection with the accession numbers CRL-1573 and CRL-10852.

Other cells may be chicken embryo fibroblast, hamster ovary cells, baby hamster kidney cells, human cervical carcinoma cells, human melanoma cells, human kidney cells, human umbilical vascular endothelium cells, human brain endothelium cells, human oral cavity tumour cells, monkey kidney cells, mouse fibroblast, mouse kidney cells, mouse connective tissue cells, mouse oligodendritic cells, mouse macrophage, mouse fibroblast, mouse neuroblastoma cells, mouse pre-B cells, mouse B lymphoma cells, mouse plasmacytoma cells, mouse teratocacinoma cells, rat astrocytoma cells, rat mammary epithelial cells, COS, CHO, BHK, 293, VERO, HeLa, MDCK, WI38, and NIH 3T3 cells.

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

The host cell culture may be cultured in any suitable culture medium. Examples of culture medium are RPMI-1640 or DMEM supplemented with, e.g., insulin, transferrin, selenium, and foetal bovine serum.

Purification

As discussed above the present invention allows a fast production of MBL. The production of MBL may be conducted by the following steps:

Fermentation—culturing of MBL expressing cells

Isolation—applying the method of the invention

Accordingly, the lectin composition may be further purified by any suitable means, either prior to the isolation applying the methods of the present invention or subsequent to the isolation according to the method of the invention. For example the lectin composition may be further purified by any physico-chemical isolating method, including but not limited to filtration methods, precipitation methods, chromatography, such as ion-exchange based on charge, gel permeation based on size, hydrophobic interaction based on hydrophobicity, or affinity chromatography.

In addition it is possible to apply the methods according to the present invention more than once within one isolation procedure. In particular, two or more different methods according to the present invention may be applied in an isolation procedure, wherein the methods may differ by the choice of solid support, choice of sugar derivative and/or choice of predetermined concentration of a sugar derivative coupled to the solid support.

For example, it is possible to perform the isolation of lectins first using a solid support which has coupled thereto a first predetermined concentration of a sugar derivative, and then performing the isolation of lectins using a solid support which has coupled thereto a second predetermined concentration of a sugar derivative, wherein the first predetermined concentration is may be higher or may be lower than the second predetermined concentration.

In particular when isolating intermediate molecular weight lectins, a two-step isolation process using at least two different solid supports with two different concentrations of sugar derivative may be used. In one example of a two-step isolation process the desired lectins are obtained in the contaminant fraction, i.e. the unbound fraction having a molecular weight below the predetermined molecular weight in the first step, for example any lectins below heptamers. In the second step the unbound fraction is applied to a different solid support having another cut-off point with respect to the predetermined molecular weight, for example binding any lectins above dimer molecular weight. Thereby the desired intermediate molecular weight composition of trimers, tetramers, pentamers and hexamers is obtained when eluting lectins bound to the second solid support. It is apparent to the person skilled in the art that the two steps of course may be conducted in the reverse order to obtain the same composition.

Functionality

The functionality of the recombinant MBL composition obtained according to the invention preferably resembles the functionality of plasma or serum MBL. In the present context the functionality of MBL means the capability of activating the complement system as discussed above in relation to functional equivalents. The functionality may be expressed as the specific activity of MBL, such as units of MBL activity per ng MBL. The functionality of the recombinant MBL composition as expressed as specific activity is preferably at least 25% of the specific activity of MBL purified from serum, such as at least 50% of the specific activity of MBL purified from serum, more preferred at least 75% of the specific activity of MBL purified from serum.

The functionality of MBL may be estimated by its capacity to form an MBL/MASP complex leading to activation of the complement system. When C4 is cleaved by MBL/MASP, an active thiol ester is exposed and C4 becomes covalently attached to nearby nucleophilic groups. A substantial part of the C4b will thus become attached to the coated plastic well and may be detected by anti-C4 antibody.

A quantitative TRIFMA for MBL functional activity was constructed by 1) coating microtitre wells with 1 mg of mannan in 100 ml of buffer; 2) blocking with Tween-20; 3) applying test samples, e.g. diluted MBL preparations 4) applying MBL deficient serum (this leads to the formation of the MBL/MASP complex); alternatively the MBL and the MBL deficient serum may be mixed before application with the microtitre wells; 5) applying purified complement factor C4 at 5 mg/ml; 6) incubate for one hour at 37° C.; 7) applying Eu-labelled anti-C4 antibody; 8) applying enhancement solution; and 9) reading the Eu by time resolved fluorometry. Between each step the plate is incubated at room temperature and washed, except between step 8 and 9.

Estimation by ELISA may be carried out similarly, e.g. by applying biotin-labelled anti-C4 in step 7; 8) apply alkaline phosphatase-labelled avidin; 9) apply substrate; and 10) read the colour intensity. A calibration curve can be constructed using dilutions of one selected normal plasma. In relation to the present invention the following serum is an example of useful serums: plasma pool LJ 6.57 28/04/97. The functionality may be expressed as the specific activity of MBL, such as in units of MBL activity per ng of MBL.

Another assay for determining a functional equivalent of MBL is to determine the ability to bind to receptor/receptors on cells.

The interaction of MBL with receptor/receptors on cells may be analysed by cytofluorimetry. 1) MBL at a concentration of 50 µg/ml is incubated with $2 \times 10^5$ cells. The binding is carried out in phosphate buffered salt solution (PBS) containing 1% FCS and 0.1% Na-azide. 2) For detection of cell-bound MBL, biotinylated anti-MBL antibody is applied; 3) followed by the addition of strepavidin-FITC and 4) analysis of the mixture by fluorimetry.

Said diseases, disorders and/or conditions in need of treatment with the compounds of the invention comprise e.g. treatment of conditions of deficiency of MBL, treatment of cancer and of infections in connection with immunosuppressive chemotherapy including in particular those infections which are seen in connection with conditions during cancer treatment or in connection with implantation and/or transplantation of organs. The invention also comprises treatment of conditions in connection with recurrent miscarriage.

Thus, in particular the pharmaceutical composition may be used for the treatment and/or prevention of clinical conditions selected from infections, MBL deficiency, cancer, disorders associated with chemotherapy, such as infections, diseases associated with human immunodeficiency virus (HIV), diseases related with congenital or acquired immunodeficiency. More particularly, chronic inflammatory demyelinating polyneuropathy (CIDP, Multifocal motoric neuropathy, Multiple sclerosis, Myasthenia Gravis, Eaton-Lambert's syndrome, Opticus Neuritis, Epilepsy; Primary antiphospholipid syndrome; Rheumatoid arthritis, Systemic Lupus erythematosus, Systemic scleroderma, Vasculitis, Wegner's granulomatosis, Sjøgren's syndrome, Juvenile rheumatiod arthritis; Autoimmune neutropenia, Autoimmune haemolytic anaemia, Neutropenia; Crohn's disease, Colitis ulcerous, Coeliac disease; Asthma, Septic shock syndrome, Chronic fatigue syndrome, Psoriasis, Toxic shock syndrome, Diabetes, Sinuitis, Dilated cardiomyopathy, Endocarditis, Atherosclerosis, Primary hypo/agammaglobulinaemia including common variable immunodeficiency, Wiskot-Aldrich syndrome and severe combined immunodeficiency (SCID), Secondary hypo/agammaglobulinaemia in patients with chronic lymphatic leukaemia (CLL) and multiple myeloma, Acute and chronic idiopathic thrombocytopenic purpura (ITP), Allogenic bone marrow transplantation (BTM), Kawasaki's disease, and Guillan-Barre's syndrome.

The route of administration may be any suitable route, such as intravenously, intramusculary, subcutanously or intradermally. Also, pulmonal or topical administration is envisaged by the present invention.

In particular the MBL composition may be administered to prevent and/or treat infections in patients having clinical symptoms associated with congenital or acquired MBL deficiency or being at risk of developing such symptoms. A wide variety of conditions may lead to increased susceptibility to infections in MBL-deficient individuals, such as chemotherapy or other therapeutic cell toxic treatments, cancer, AIDS, genetic disposition, chronic infections, and neutropenia.

It appears that cancer patients treated by chemotherapy are often susceptible to infection due to adverse effects of the drug regime on cells of the immune system, which is the background for the use of MBL therapy in the treatment of this condition. The observed low plasma concentrations of MBL (below 500 ng/ml) are indicative of an increased susceptibility to clinical significant infections, and the immune defence of these patients can be reinforced by administration of recombinant or natural plasma-derived MBL.

The pharmaceutical composition may thus be administered for a period before the onset of administration of chemotherapy or the like and during at least a part of the chemotherapy.

The MBL composition may be administered as a general "booster" before chemotherapy, or it may be administered to those only being at risk of developing MBL deficiency. The group of patients being at risk may be determined by measuring the MBL level before treatment and only subjecting those to treatment whose MBL level is below a predetermined level. The limit for determining a low MBL level is evaluated to be below 500 ng/ml for most groups. The MBL level may be determined by time resolved immunofluorescent assay as described in Example 9, ELISA, RIA or nephelometry.

Another indication for administering MBL is when the MBL level is below 50% of the normal level, such as below 300 ng/ml, or below 200 ng/ml.

The MBL composition is administered in suitable dosage regimes, in particularly it is usually administered at suitable intervals, e.g. once or twice a week during chemotherapy.

Normally from 1–100 mg is administered per dosage, such as from 2–10 mg, mostly from 5–10 mg per dosage.

Mostly about 0.1 mg/kg body weight is administered.

Thus, in one aspect the invention concerns MBL, including rMBL, fragments or mimics hereof for use in the treatment of cancer and of conditions of diseases and disorders of e.g. the immune system and reproductive system, said treatment consisting of creation, reconstitution, enhancing and/or stimulating the opsonic and/or bactericidal activity of the complement system, i.e. enhancing the ability of the immune defence to recognise and kill microbial pathogens.

Furthermore, an aspect of the present invention is the use of a recombinant composition according to the present invention in a kit-of-parts further comprising another medicament. In particular the other medicament may be an anti-microbial medicament, such as antibiotics.

Concerning miscarriage, it has been reported that the frequency of low plasma levels of MBL is increased in patients with otherwise not explained recurrent miscarriages, which is the background for lowering of the susceptibility to miscarriage by a reconstitution of the MBL level by administration of recombinant MBL in these cases.

As to the nature of compounds of the invention, it appears that in its broad aspect, the present invention relates to compounds which are able to act as opsonins, that is, able to enhance uptake by macrophages either through direct interaction between the compound and the macrophage or through mediating complement deposition on the target surface. A particular example hereof is MBL, a fragment or a mimic hereof. The present invention is based upon the disclosure of a synthesis of a recombinant human MBL which appears to be closer to the structure of the natural human MBL than achieved in the past.

The invention has now been explained and accounted for in various aspects and in adequate details, but additionally it will be illustrated below by the non-limiting examples of preferred embodiments.

EXAMPLES

Example 1

Purification of MBL Using an Immobilized Amino Sugar

MBL was recombinantly produced by human cell lines like a HEK293 based cell line comprising an expression construct encoding MBL as described in WO 00/70043, in an HyQ based media (HyClone), and MBL was subsequently purified by affinity chromatography by using an immobilized amino sugar.

A D-mannosamine column was prepared by coupling 1.0 g of D-mannosamine (ICN Biomedicals, Cat. no.102252) to 13.5 mL suspended NHS-activated Sepharose FF (Amersham Biosciences, Cat. no.17-0906-02).

Coupling conditions were exactly as described in the vendor's instructions for the NHS-activated gel: First, the resin was washed with ice-cold 1 mM HCl. Subsequently, the resin was incubated with the amino sugar (100 mg/mL D-mannosamine, 10 mM $NaH_2PO_4$, pH=7.0) overnight at 4° C. Next day the resin was blocked with ethanolamine buffer (100 mM, pH 7.0), and packed into a HR10/10 column. Finally, the column was equilibrated 3 times with a weak Tris buffer (pH 7.4) and a weak acetate buffer (pH=3.1) in an alternating pattern.

One litre of cell culture broth was added to the column, and eluted using an EDTA containing buffer.

An MBL specific immunoassay of the corresponding application, run-through, and eluting main peak reveals that MBL is almost entirely found in the eluting main peak (FIG. 1). MBL content is easily verified by a chromatographic technique, such as size exclusion chromatography on Superose 6 (prepacked HR 10/30 from Amersham Biosciences), or MALDI-MS investigations after reduction.

Example 2

Purification of a Selected Size-fraction of MBL Using an Immobilized Amino Sugar Selected fractions of lectin oligomers may be obtained by adjusting the amino sugar ligand concentration.

A resin with relatively low ligand concentration was made by coupling 0.1 g of D-mannosamine (Sigma, Cat. no.M4670) to 12.5 mL suspended NHS-activated Sepharose FF (Amersham Biosciences, Cat. no.17-0906-02).

A similar resin with relatively high ligand concentration was made by coupling 1.0 g of D-mannosamine (Sigma, Cat. no.M4670) to 12.5 mL suspended NHS-activated Sepharose FF (Amersham Biosciences, Cat. no.17-0906-02).

A 'dummy' column with no ligand was made by using a coupling buffer without the amino sugar during the coupling to 12.5 mL suspended NHS-activated Sepharose FF (Amersham Biosciences, Cat. no.17-0906-02).

In all cases, coupling conditions were exactly as described in the vendor's instructions for the NHS-activated gel. One litre of cell culture broth (made as described in Example 1) is added to each column, and eluted using an EDTA containing buffer. An MBL specific immunoassay of the corresponding application, run-through, and eluting main peak reveals that MBL is almost entirely found in the eluting main peak from the column with high ligand concentration ('high-sub' column).

A selected high-mass fraction of MBL is found in the eluting main peak from the column with low ligand concentration ('low-sub' column), and the remaining MBL is seen in the run-through fraction. All MBL is found in run through fraction of the 'dummy' column, showing that the MBL affinity is ligand specific (FIG. 2).

Example 3

Purification of a Selected Size-fraction of MBL Using a Series of Columns with Immobilized Amino Sugars Specific fractions of lectin oligomers are obtained by applying a series of columns with different ligand concentrations.

One litre of cell culture broth (made as described in Example 1) is added to two columns in series: The first column is a column with a low amino sugar ligand concentration (a 'low-sub' column as described in Example 2), while the second is a column with a high amino sugar ligand concentration (a 'high-sub' column as described in Example 2).

The run-through fraction of MBL from the 'low-sub' column is captured on the 'high-sub' column. Each column is then eluted with EDTA buffer (50 mM, pH 7.4). The eluting fraction from the 'low-sub' column contains the high mass size MBL with a mean size distribution higher than the original application. The eluting fraction from the 'high-sub' column contains a fraction of MBL with mass less than the 'low sub' column eluate, but without low mass size MBL, like monomeric MBL or dimeric MBL.

Example 4

Purification of a Plasma Derived MBL Using an Immobilized Amino Sugar

Lectins from plasma might be purified using immobilized amino sugars.

A D-mannosamine column is prepared as described in Example 1. One half litre of blood plasma is obtained from a blood bank, and coagulated by weak heating after addition of $CaCl_2$. The obtained serum is added to the column, and after a short wash protein is eluted using an EDTA containing buffer. An MBL specific immunoassay of the corresponding application, run-through, and eluting main peak reveals that MBL is almost entirely found in the eluting main peak from the column.

MBL content is easily verified by a chromatographic technique, such as size exclusion chromatography on Superose 6 (prepacked HR 10/30 from Amersham Biosciences), anion exchange chromatography on MonoQ (HR 5/5 from APBiotech), or MBL ELISA (Statens Serum Institute, Copenhagen).

Example 5

Purification of MBL Using Immobilized Amino Sugars Other than D-mannosamine Immobilized D-mannosamine may be exchanged with any amino sugar capable of binding the lectin after immobilization via the $NH_2$ group. The same effects of ligand concentration are seen.

A resin with relatively low ligand concentration was made by coupling 0.1 g of D-glucosamine (Sigma, Cat. no.G4875) to 12.5 mL suspended NHS-activated Sepharose FF (Amersham Biosciences, Cat. no.17-0906-02). A similar resin with relatively high ligand concentration was made by coupling 1.0 g of D-glucosamine (Sigma, Cat. no.G4875) to 12.5 mL suspended NHS-activated Sepharose FF (Amersham Biosciences, Cat. no.17-0906-02). In both cases, coupling conditions were exactly as described in the vendor's instructions for the NHS-activated gel.

One litre of cell culture broth (made as described in Example 1) is added to each column, and eluted using an EDTA containing buffer.

An MBL specific immunoassay of the corresponding application, run-through, and eluting main peak reveals that MBL is almost entirely found in the eluting main peak from the column with high ligand concentration ('high-sub' column) (FIG. 3).

Example 6

Large Scale Purification of Lectins Using an Immobilized Amino Sugar

The affinity chromatography is easily scaled up ten times.

A large D-glucosamine column is prepared by coupling 5.0 g of D-glucosamine (Sigma, Cat. no.G4875) to 100 mL suspended NHS-activated Sepharose FF (Amersham Biosciences, Cat. no.17-0906-02). Coupling conditions were exactly as described in the vendor's instructions for the NHS-activated gel. Ten litres of cell culture broth with recombinantly produced MBL are added to the column, and eluted using an EDTA containing buffer.

An MBL specific immunoassay of the corresponding application, run-through, and eluting main peak reveals that MBL is almost entirely found in the eluting main peak. MBL content is easily verified by chromatographic techniques, such as size exclusion chromatography on Superose 6 (prepacked HR 10/30 from Amersham Biosciences), anion exchange chromatography on MonoQ (Amersham Biosciences), SDS-PAGE with westerns using Hyb131-01 (Statens Serum Institute), MBL specific ELISA's (Statens Serum Institute), amino acid composition analysis, and MALDI-MS investigations after reduction.

Example 7

Detection of Lectins Using Immobilized Amino Sugars

Amino sugars can be immobilized to microtiter wells and be applied for detection of lectins.

D-glucosamine is coupled to microtiter wells (Cyanuric chloride activated CovaLink $NH_2$ from Life Technologies) by incubating the wells with 1.0 µg amino sugar per well overnight, as described by vendor. Dilutions of MBL containing samples are added to the wells and incubated for 3 hours at room temperature. Subsequently a detection antibody like Hyb131-01 (Statens Serum Institute) is applied for 3 hours at room temperature, followed by incubation with a HRP- or AP-labelled secondary antibody (anti-IgG, Dako) for 1 hour. After addition of the enzyme substrate, the amount of MBL is estimated in an ELISA reader.

The invention claimed is:

1. A method for isolating at least one lectin from a preparation comprising a variety of lectin molecules, comprising
   providing a solid support which is derivatized with a predetermined concentration of an amino sugar having a primary amino group, said amino sugar being coupled through the amino group to the solid support,
   applying the preparation to said solid support,
   allowing the lectins to bind to the sugar coupled to the solid support,
   washing the solid support, with a washing liquid removing unbound contaminants, and
   optionally recovering said lectin(s) from the solid support.

2. The method according to claim 1, wherein the amino sugar is selected from the group consisting of galactosamine, mannosamine, glucosamine, allosamine, altrosamine, ribosamine, arabinosamine, gulosamine, idosamine, fucosamine, talosamine, xylosamine, lyxosamine, sorbosamine, tagatosamine, psicosamine and fructosamine.

3. The method according to claim 1, wherein the amino sugar is selected from the group consisting of D-mannosamine, D-glucosamine, D-allosamine, D-altrosamine, D-ribosamine, D-arabinosamine, L-gulosamine, L-idosamine, L-galactosamine, L-fucosamine, L-talosamine, L-xylosamine and L-lyxosamine.

4. The method according to claim 1, wherein the amino sugar is selected from the group consisting of D-mannosamine and D-glucosamine.

5. The method according to claim 1, wherein the lectin is recovered from said solid support.

6. The method according to claim 5, wherein the lectin is recovered in substantially pure form.

7. The method according to claim 1, wherein the solid support is selected from the group consisting of chromatography columns, chromatographic resins, filters, plastic surfaces, glass surfaces and magnetic particles.

8. The method according to claim 7, wherein the column is selected from the group consisting of N-hydroxy succinimide activated resins, Cyanogen bromide activated resins, Epoxy activated resins, ECH Sepharose 4B from Amersham Biosciences and Activated CH-Sepharose 4B from Amersham Biosciences.

9. The method according to claim 7, wherein the plastic surface is an activated microtiter plate.

10. The method according to claim 1, wherein the lectin is mannose-binding lectin (MBL).

11. The method according to claim 1, wherein the washing liquid comprises one or more components selected from the group consisting of sugars capable of binding to the lectin, sugar derivatives capable of binding to the lectin and divalent metal ion chelating agents.

12. The method according to claim 11, wherein the sugar is selected from the group consisting of mannose, mannosamine, N-acetylmannosamine, glucose, glucosamine, N-acetylglucosamine, fructose, fructosamine, N-acetylfructosamine, galactose, galactosamine, N-acetylgalactosamine, saccharose and maltose.

13. A method for increasing the ratio R of a composition comprising a variety of lectin molecules, wherein R is the ratio of the concentration of lectin molecules having a high molecular weight above a predetermined molecular weight to the concentration of lectin molecules having a low molecular weight below or equal to the predetermined molecular weight, said method comprising
obtaining a lectin preparation comprising low molecular weight lectin and high molecular weight lectin, said preparation having the ratio $R=R_0$,
applying the preparation to an isolation method as defined in claim 1,
obtaining a composition comprising the recovered lectin molecules.

14. A method for producing a composition comprising a variety of lectin molecules, wherein substantially all of said lectin molecules have a molecular weight above a predetermined molecular weight for dimer lectins, said method comprising
obtaining a lectin preparation comprising lectin molecules having a high molecular weight above the predetermined molecular weight and lectin molecules having a low molecular weight below or equal to the predetermined molecular weight, wherein the predetermined molecular weight is the molecular weight of dimeric mannose-binding lectin (MBL), which is about 200 kDa as determined by SDS-page,
applying the method as defined in claim 1 to said preparation,
obtaining a composition comprising the recovered lectin molecules.

15. A method for separating a composition comprising a variety of lectin molecules, wherein substantially all of said lectin molecules have a high molecular weight above a predetermined molecular weight, from a lectin preparation comprising lectin molecules having a high molecular weight above the predetermined molecular weight and lectin molecules having a low molecular weight below or equal to the molecular weight for dimer lectins, wherein the predetermined molecular weight is the molecular weight of dimeric mannose-binding lectin (MBL), which is about 200 kDa as determined by SDS-page,
obtaining said lectin preparation,
applying the method as defined in claim 1 to said preparation,
obtaining a composition comprising the recovered lectin molecules.

16. A method for producing a composition comprising a variety of lectin molecules, wherein substantially all of said lectin molecules have a low molecular weight below or equal to a predetermined molecular weight, said method comprising
obtaining a lectin preparation comprising lectin molecules having a high molecular weight above the predetermined molecular weight and lectin molecules having a low molecular weight below or equal to the predetermined molecular weight,
applying the method as defined in claim 1 to said preparation,
obtaining a composition comprising the unbound lectin molecules of the washing liquid.

17. A method of increasing the ratio R' of a preparation comprising a variety of lectin molecules,
wherein R' is the ratio of the concentration of lectins having an intermediate molecular weight to the combined concentration of lectin molecules having a high molecular weight and a low molecular weight,
wherein intermediate molecular weight is a molecular weight below a first predetermined molecular weight and above a second predetermined molecular weight, high molecular weight is a molecular weight above or equal to the first predetermined molecular weight and low molecular weight is a molecular weight below or equal to the second predetermined molecular weight,
said method comprising the steps of
a) obtaining a lectin preparation comprising low molecular weight lectin, intermediate molecular weight lectin and high molecular weight lectin, and
b) applying the method as defined in claim 1 to said preparation; and
c) obtaining a composition comprising the recovered lectin molecules whereby the value of the ratio R' for the composition of (c) is higher than the value of the ratio R' for the preparation of (a); and
d) optionally repeating step b).

18. The method according to claim 13, wherein the lectin is mannose-binding lectin (MBL).

19. The method according to claim 18, wherein at least 50% of the high molecular weight MBL of the composition has a molecular weight above 200 kDa.

20. The method according to claim 18, wherein the low molecular weight MBL comprises MBL having a molecular weight below 200 kDa.

21. The method according to claim 1, wherein the lectin preparation is a recombinant mannose-binding lectin (MBL), preparation.

22. The method according to claim 21, wherein the MBL preparation is obtained by
preparing a gene expression construct encoding human MBL peptide or a functional equivalent thereof,
transforming a host cell culture with the construct,
cultivating the host cell culture in a culture medium, thereby obtaining expression and secretion of the polypeptide into the culture medium,
obtaining a preparation comprising a variety of MBL molecules.

23. The process according to claim 22, wherein the gene expression construct comprises at least one intron sequence from the human MBL gene or a functional equivalent thereof.

24. The process according to claim 23, wherein the gene expression construct comprises at least two exon sequences from the human MBL gene or a functional equivalent thereof.

25. The process according to claim 22, wherein the gene expression construct comprises a cDNA sequence encoding a MBL subunit or a functional equivalent thereof.

26. The process according to claim 22, wherein the host cell culture is cultured in vitro.

27. The process according to claim 22, wherein the host cell culture is a eukaryotic host cell culture.

28. The process according to claim 22, wherein the host cell culture is a mammalian host cell culture.

29. A solid support, wherein said solid support is a chromatography column resin, and wherein said solid support has, covalently coupled thereto, a predetermined concentration of 0.1 mg to 1000 mg amino sugar per ml resin, said amino sugar having a primary amino group, said amino sugar being coupled through the amino group to the solid support.

30. The solid support according to claim 29, wherein the amino sugar is selected from the group consisting of galactosamine, fucosamine, mannosamine, glucosamine, allosamine, altrosamine, ribosamine, arabinosamine, gulosamine, idosamine, galactosamine, talosamine, xylosamine, lyxosamine, sorbosamine, tagatosamine, psicosamine and fructosamine.

31. The solid support according to claim 29, wherein the solid support is selected from the group consisting of chromatography columns, chromatographic resins, filters, plastic surfaces, glass surfaces and magnetic particles.

32. The solid support according to claim 29, wherein the column is selected from the group consisting of N-hydroxy succinimide activated resins, Cyanogen bromide activated resins, Epoxy activated resins, ECH Sepharose 4B from APBiotech and Activated CH-Sepharose 4B from AP-Biotech.

33. A method for isolating at least one lectin from a preparation comprising a variety of lectin molecules, comprising
providing a solid support which is derivatized with at least one amino sugar, said amino sugar having a primary amino group,
applying the preparation to said solid support,
allowing the lectins to bind to the amino sugar coupled to the solid support,
washing the solid support with a washing liquid removing unbound contaminants, and
optionally recovering said lectin(s) from the solid support.

34. The method according to claim 33, wherein the amino sugar is selected from the group consisting of galactosamine, mannosamine, glucosamine, allosamine, altrosamine, ribosamine, arabinosamine, gulosamine, idosamine, fucosamine, talosamine, xylosamine, lyxosamine, sorbosamine, tagatosamine, psicosamine and fructosamine.

35. The method according to claim 33, wherein the amino sugar is selected from the group consisting of D-mannosamine, D-glucosamine, D-allosamine, D-altrosamine, D-ribosamine, D-arabinosamine, L-gulosamine, L-idosamine, L-galactosamine, L-fucosamine, L-talosamine, L-xylosamine and L-lyxosamine.

36. The method according to claim 33, wherein the amino sugar is selected from the group consisting of D-mannosamine and D-glucosamine.

37. The method according to claim 33, wherein the lectin is recovered from said solid support.

38. The method according to claim 33, wherein the lectin is recovered in substantially pure form.

39. The method according to claim 33, wherein the solid support is selected from the group consisting of chromatography columns, chromatographic resins, filters, plastic surfaces, glass surfaces and magnetic particles.

40. The method according to claim 33, wherein the column is selected from the group consisting of N-hydroxy succinimide activated resins, Cyanogen bromide activated resins, Epoxy activated resins, ECH Sepharose 4B from Amersham Biosciences and Activated CH-Sepharose 4B from Amersham Biosciences.

41. The method according to claim 33, wherein the plastic surface is an activated microtiter plate.

42. The method according to claim 33, wherein the lectin is mannose-binding lectin (MBL).

43. The method according to claim 33, wherein the washing liquid comprises one or more components selected from the group consisting of sugars capable of binding to the lectin, sugar derivatives capable of binding to the lectin and divalent metal ion chelating agents.

44. The method according to claim 33, wherein the sugar is selected from the group consisting of mannose, mannosamine, N-acetylmannosamine, glucose, glucosamine, Nacetylglucosamine, fructose, fructosamine, N-acetylfructosamine, galactose, galactosamine, N-acetylgalactosamine, saccharose and maltose.

45. The method according to claim 1, wherein the amino sugar comprises an MBL binding site and the lectin is mannose-binding lectin (MBL).

46. The method of claim 14, wherein said composition comprising the recovered lectin molecules is further characterized by a ratio ($R_1$) of the concentration of the lectin molecules having a molecular weight above the predetermined molecular weight, to the concentration of the lectin molecules having a concentration below the predetermined molecular weight, such that $R_1$ is at least 1.

47. The method of claim 15, wherein said composition comprising the recovered lectin molecules is further characterized by a ratio ($R_1$) of the concentration of the lectin molecules having a molecular weight above the predetermined molecular weight, to the concentration of the lectin molecules having a concentration below the predetermined molecular weight, such that $R_1$ is at least 1.

* * * * *